United States Patent [19]

Schmitt et al.

[11] Patent Number: 5,415,852
[45] Date of Patent: * May 16, 1995

[54] PROCESS FOR FORMING A DINITRAMIDE SALT OR ACID BY REACTION OF A SALT OR FREE ACID OF AN N(ALKOXYCARBONYL)N-NITROAMIDE WITH A NITRONIUM-CONTAINING COMPOUND FOLLOWED BY REACTION OF THE INTERMEDIATE PRODUCT RESPECTIVELY WITH A BASE OR ALCOHOL

[75] Inventors: Robert J. Schmitt, Redwood City; Jeffrey C. Bottaro, Mountain View; Paul E. Penwell, Menlo Park; David C. Bomberger, Belmont, all of Calif.

[73] Assignee: SRI International, Menlo Park, Calif.

[*] Notice: The portion of the term of this patent subsequent to Mar. 30, 2010 has been disclaimed.

[21] Appl. No.: 968,928

[22] Filed: Oct. 30, 1992

Related U.S. Application Data

[63] Continuation-in-part of Ser. No. 827,247, Jan. 29, 1992, abandoned.

[51] Int. Cl.$^6$ ............................................. C01F 17/00
[52] U.S. Cl. ................................... 423/385; 423/387; 564/107; 564/109
[58] Field of Search ................. 423/385, 387; 564/107, 564/109

[56] References Cited

U.S. PATENT DOCUMENTS

| | | | |
|---|---|---|---|
| 2,772,306 | 11/1956 | Thomas | 260/482 |
| 2,978,493 | 4/1961 | Frankel | 260/482 |
| 3,258,478 | 6/1966 | Baum | 260/482 |
| 3,423,419 | 1/1969 | Grakauskas et al. | 260/308 |
| 3,428,667 | 2/1969 | Hamel et al. | 260/467 |
| 3,687,954 | 8/1972 | Tyler, III et al. | 260/268 R |
| 4,338,442 | 7/1982 | Strecker | 544/215 |
| 4,878,968 | 11/1989 | Willer et al. | 149/45 |
| 5,198,204 | 3/1993 | Bottaro et al. | 423/385 |
| 5,254,324 | 10/1993 | Bottaro et al. | 423/263 |
| 5,316,749 | 5/1994 | Schmitt et al. | 423/385 |

OTHER PUBLICATIONS

*Chemical & Engineering News,* Jan. 17, 1994, pp. 18–19.
Barbes, Henri et al., "Relation Between Nitration Capacity and Structure of $NO_2+$ in Some Nitryl Salts", *Revue de Chemie Minerale,* vol. 8, No. 6, 1971, pp. 851–858.
Barbes et al., *Chem. Abs.,* 76, p. 459, abs. #78689v (1972).
Leroy, Geroges, et al., "A Theoretical Investigation of the Structure and Reactivity of Nitrogen–Centered Radicals", *Journal of Molecular Structure (Theochem),* vol. 153, 1987, Table 6.
Tellier-Pollon, Sylvaine, et al., "Inorganic Preparation of Nitramide", *Revue de Chemie Minerale,* vol. 4, No. 2, 1967, pp. 413–423.
Tellier-Pollon et al., *Chem. Abs.,* 68, p. 7193, abs. #74757c (1968).
(List continued on next page.)

*Primary Examiner*—Edward A. Miller
*Attorney, Agent, or Firm*—John P. Taylor

[57] ABSTRACT

A method is disclosed for forming an ionically bonded dinitramide salt or acid useful as a stable oxidizer for solid fuel rocket propellant or explosive formulations is disclosed. The dinitramide salt is formed by the reaction of an N(alkoxycarbonyl)N-nitroamide and a nitronium-containing compound, at a temperature of from about $+60°$ C. to about $-120°$ C., followed by contacting the reaction mass with a base to form the dinitramide salt, or an alcohol to form the corresponding dinitramidic acid. The N(alkoxycarbonyl)N-nitroamide may be formed by first mixing the corresponding alkylcarbamate with an anhydride of one or more 1–20 carbon organic acids, then adding nitric acid to the reaction mixture. If the salt of the N(alkoxycarbonyl)N-nitroamide is to be formed, a base is then added until the pH reaches about 7-10. The nitronium-containing reactant may be a covalently bonded compound containing a $NO_2-$ group; a nitryl halide; or a nitronium salt having the formula $(NO_2^+)_q X^{-q}$, where X is the anion of the nitronium salt and $q=1-2$.

31 Claims, 1 Drawing Sheet

OTHER PUBLICATIONS

"Third Quarterly Report: Basic Research in Solid Oxygen Oxidizers", Government Contract AF 04(611)–8549, Dec. 1963, pp. 6–7.

Vast, Pierre, et al., "Reaction Between Nitric Anhydride and Ammonia at Low Temperature, Characterization of Nitramide", *Compt. Rend.*, vol. 260, No. 22, (Groupe 8), 1965, pp. 5799–5801.

Vast et al., *Chem. Abs.*, 63, abs. #5224c, (1965).

Vast, Pierre et al., "Reactions Between Liquid Ammonia and Some Nitryl Salts:," *C. R. Acad. Sci. Paris*, Ser. C264 (21), 1967, pp. 1697–1699.

Vast et al., *Chem. Abs.*, 67, abs. #50007m, p. 4677 (1967).

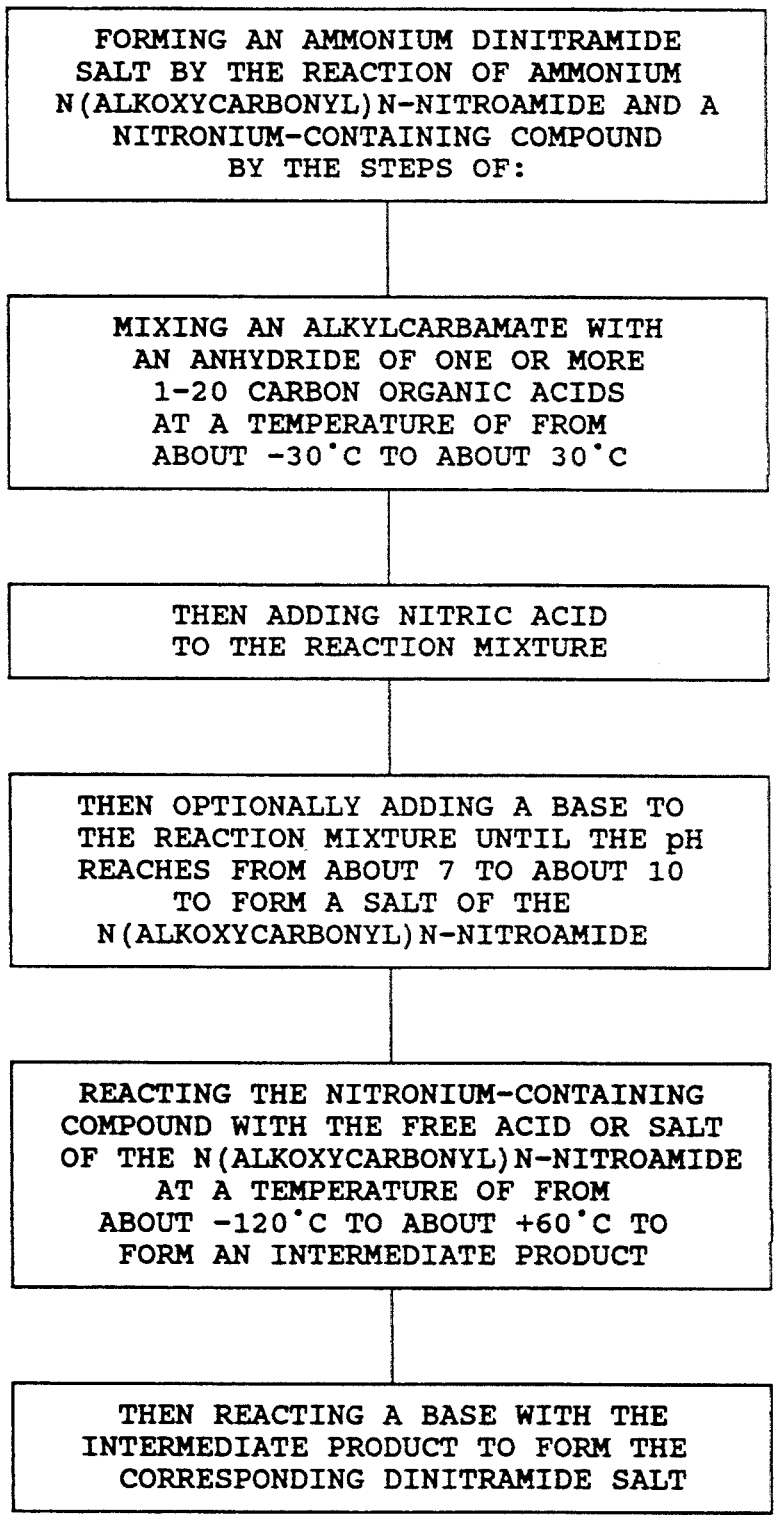

5,415,852

PROCESS FOR FORMING A DINITRAMIDE SALT OR ACID BY REACTION OF A SALT OR FREE ACID OF AN N(ALKOXYCARBONYL)N-NITROAMIDE WITH A NITRONIUM-CONTAINING COMPOUND FOLLOWED BY REACTION OF THE INTERMEDIATE PRODUCT RESPECTIVELY WITH A BASE OR ALCOHOL

GOVERNMENT RIGHTS

This invention was made under government contracts N00014-86-C-0699 and N00014-88-C-0537 of the Office of Naval Research; and the government of the United States, therefore, has rights in this invention.

CROSS-REFERENCE TO RELATED APPLICATIONS

This application is a continuation-in-part of application Ser. No. 07/827,247, filed Jan. 29, 1992, now abandoned.

BACKGROUND OF THE INVENTION

1. Field of the Invention

This invention relates to a process for forming a dinitramide salt, or dinitramidic acid, by reaction of a salt or free acid of an N(alkoxycarbonyl)N-nitroamide and a nitronium-containing compound such as $N_2O_5$, a nitryl halide, or a nitronium salt to form an intermediate product, which is then reacted with a base to form the dinitramide salt, or with an alcohol to form dinitramidic acid.

2. Description of the Related Art

Solid oxidizers, such as ammonium perchlorate or potassium perchlorate, have been used in the past in rocket propellant formulation because of their improved ease of storage over liquid oxidizers. However, the presence of a halogen in the solid oxidant produces a visually observable smoke trail which is also observable on radar as well. Also, chlorine poses a serious atmospheric environmental hazard of ozone depletion and acid rain.

Because of such shortcomings in the use of perchlorate solid fuel oxidizers, other materials, including nitrate ($NO_3^-$) compounds, have been investigated in the search for oxidizers which would provide the desired energy density and stability, without the drawbacks of the perchlorate oxidants.

In related application Ser. No. 07/540,020, filed by several of us on Jun. 18, 1990, now issued as U.S. Pat. No. 5,254,324 on Oct. 19, 1993, and assigned to the assignee of this invention and cross-reference to which is hereby made, we disclosed and claimed new ionically bound compounds suitable for use as oxidizers in rocket propellants. These compounds comprise dinitramide salts of metals or nitrogen-containing cations. We also described and claimed in that application a method of making such nitramide salts by first forming a dinitramine compound and then reacting the dinitramine compound with either a nitrogen-containing compound or a metal salt.

In related application Ser. No. 07/539,647, also filed by several of us on Jun. 18, 1990 and assigned to the assignee of this invention and cross-reference to which is hereby made, we disclosed and claimed another method of forming the dinitramide salts of metals or nitrogen-containing cations claimed in application Ser. No. 07/540,020. This second method of making such nitramide salts comprises nitrating a carbamate to form a dinitramide acid intermediate product, followed by neutralizing the intermediate product with a compound selected from the class consisting of ammonia, hydrazine, a primary amine, a secondary amine, and a salt having the formula AX where A is a metal ion or a nitrogen-containing ion and X is a fluoride, chloride, hydroxyl, carbonate, alkoxide, or carboxyl anion.

In related application Ser. No. 07/737 757, filed by us with another on Jul. 30, 1991, now issued as U.S. Pat. No. 5,316,749 on May 31, 1994, and assigned to the assignee of this invention and cross-reference to which is hereby made, we disclosed and claimed yet another method of forming ammonium dinitramide salt by the reaction of ammonia and a nitronium-containing compound such as nitronium tetrafluoroborate or nitronium nitrate.

It is also known to react a nitronium salt with an organic nitramine to form a covalently bonded N,N-dinitramine compound. Hamel et al. U.S Pat. No. 3,428,667 describes the reaction of an ionic nitronium salt with a primary organic nitramine to form N,N-dinitramines having the general formula $R-[N(NO_2)_2]_n$ where n is 1–2 and R is a monovalent or divalent organic radical. These compounds are said to be highly energetic and useful as ingredients in propellant, explosive, and pyrotechnic compositions.

However, as discussed in our related applications, the formation and use of covalently bonded nitrogen-containing solid fuel oxidizing agents for use in rocket propellant formulations is not as desirable as the use of the previously claimed dinitramide salts because these salts have been found to be much more stable. The processes for forming such stable dinitramide salts in the aforementioned U.S. Pat. Nos. 5,254,324 and 5,198,204 have been multiple step processes involving the formation of precursors which must then be isolated or recovered for a further reaction with another reactant to form the desired ionically bonded dinitramide salt product. It would be desirable to provide a simplified process to form an ionically bonded stable dinitramide salt wherein one reaction vessel may be used to form the dinitramide salt product.

It would also be desirable to provide a method for the formation of such dinitramide salts which would provide a high yield, i.e., ~50%, while only using one mole of nitronium reactant per mole of other reactant, as opposed to the method described in U.S. Pat. No. 5,316,749, wherein the desired ammonium dinitramide salt is formed by reacting one mole of ammonia with two moles of nitronium-containing compound.

SUMMARY OF THE INVENTION

It is, therefore, an object of this invention to provide a simplified process for the formation of a dinitramide salt by the reaction of a salt or free acid of a N(alkoxycarbonyl)N-nitroamide and a nitronium-containing compound, such as a nitronium salt, a nitryl halide, or a covalently bonded compound, at a temperature which will result in the formation of an alkoxycarbonyl N,N-dinitramine intermediate product which can be reacted with a base or an alcohol to respectively give the dinitramide salt or acid.

More particularly, it is an object of the invention to provide a process for forming a dinitramide salt by the reaction of a salt or free acid of an N(alkoxycarbonyl)N-nitroamide and a nitronium-containing compound at a temperature which ranges from about +60° C. to about −120° C., preferably from about 0° C. to about −90° C., and most preferably from about −20° C. to about −80° C.

It is a further object of the invention to provide an improved process for forming the salt or free acid of an N(alkoxycarbonyl)N-nitroamide, which reactant may then be used in the process for forming the dinitramide salt by reaction with the nitronium-containing reactant, by first mixing an alkylcarbamate with the anhydride of one or more 1–20 carbon organic acids, then adding nitric acid, and then (if a salt is desired rather than the free acid) adding an appropriate base, while maintaining the reaction temperature at a range of from about −30° C. to about 60° C., preferably about 0° C.

These and other objects of the invention will be apparent from the following description and accompanying flow sheet.

BRIEF DESCRIPTION OF THE DRAWING

The sole drawing is a flowsheet illustrating the process of the invention.

DETAILED DESCRIPTION OF THE INVENTION

The invention comprises a simplified method of forming a dinitramide salt having the formula $M^{+n}(N(NO_2)_2^-)_n$, where M is selected from the group consisting of a metal ion, hydrogen, and a nitrogen-containing cation having from 1 to 8 nitrogen atoms and n is the cationic charge of M, usually 1–3. The dinitramide salt is useful as a stable oxidizer for solid fuel rocket propellant or explosive formulations.

When the $M^{+n}$ ion is a metal ion, it may include ions of metals such as alkali metals, e.g., Li, Na, K, Rb, and Cs; alkaline earth metals, e.g., Be, Ca, Ba, Sr, and Mg; Group Ib metals, e.g., Ga, In, and the Lanthanide elements (57–71); Group IV metals, e.g., Ti, Zr, Hf, Ge, and Sn; Group V metals, e.g., V, Nb, and Ta; Group VI metals, e.g., Cr, Mo, and W; Group VIIa metals, e.g., Mn, Tc, and Re; and Group VIII metals, e.g., Fe, Co, Ni, Ru, Rh, Pd, Os, Ir, and Pt. Of the foregoing metal ions, Li, Na, K, Ba, and Mg are preferred metal ions.

When the $M^{+n}$ ion is a 1–2 nitrogen-containing cation, it may have the formula $R_kH_mN_x^+$, wherein $x=1$ to 2, $k=0$ to $3+x$, $m=3+x-k$, and each R is the same or different 1–6 carbon straight chain or branched alkyl. Examples of such ions include $NH_4^+$, $CH_3NH_3^+$, $(CH_3)_2NH_2^+$, $(CH_3)_3NH^+$, $(CH_3)_4N^+$, $C_2H_5NH_3^+$, $(C_2H_5)_2NH_2^+$, $(C_2H_5)_3NH^+$, $(C_{25})_4N^+$, $(C_2H_5)(CH_3)NH_2^+$, $(C_2H_5)(CH_3)_2NH^+$, $(C_2H_5)_2(CH_3)_2N^+$, $(C_3H_7)_4N^+$, $(C_4H_9)_4N^+$, $N_2H_5^+$, $CH_3N_2H_4^+$, $(CH_3)_2N_2H_3^+$, $(CH_3)_3N_2H_2^+$, $(CH_3)_4N_2H^+$, $(CH_3)_5N_2^+$, etc.

The $M^{+n}$ ion may also comprise a cubane-1,4-bis ammonium ion, such as described in the aforementioned Willer et al. U.S. Patent 4,878,968, cross-reference to which is hereby made; a cubane-1,2,4,7-tetra ammonium ion; a cubane-1,3,5,7-tetra ammonium ion; a cubane-1,2,3,4,-tetra ammonium ion; a cubane-1,2,3,4,7-penta ammonium ion; or a cubane-1,2,4,6,8penta ammonium ion.

Other nitrogen-containing cations which may comprise the $M^{+n}$ ion include guanidium $(C(N_2)_3^+)$; triaminoguanidinium $(C(N_2H_3)_3^+)$; nitronium $(O=N=O^+)$; nitrosonium $(N\equiv O^+)$; and a 1–10,000 nitrogen polymer of ethyleneimine, if an appropriately low reaction temperature is used.

The ionically bonded dinitramide salt is formed by the reaction of the salt or free acid of an N(alkoxycarbonyl)N-nitroamide and a nitronium-containing compound, such as a nitronium salt, a nitryl halide, or a covalently bonded compound containing a $NO_2-$ group, at a temperature which ranges from about +60° C. to about −120° C., preferably ranges from about +60° C. to about −90° C., and most preferably ranging from about −20° C. to about −80° C.; followed by the step of treating the intermediate product formed in the first reaction with a base to obtain the desired dinitramide salt, e.g., treating with ammonia to form the ammonium dinitramide salt; or by treating the intermediate product with an alcohol to form the corresponding dinitramidic acid.

a. The Salt or Free Acid N(alkoxycarbonyl)N-nitroamide Reactant

The salt or free acid N(alkoxycarbonyl)N-nitroamide reactant used in the process has either the formula $M^{+n}((O_2NNCO_2R)^-)_n$, where M is selected from the group consisting of a metal ion, hydrogen, and a nitrogen-containing cation having from 1 to 8 nitrogen atoms, n is the cationic charge of M (usually 1-3), and R is selected from the group consisting of a 1–20 carbon branched or straight chain alkyl and a 1–20 carbon branched or straight chain fluoroalkyl; or the formula $(M^{+n}((O_2NNCO_2)^-)_n)_rR'$ where M is selected from the group consisting of a metal ion, hydrogen, and a nitrogen-containing cation having from 1 to 8 nitrogen atoms, n is the cationic charge of M (usually 1-3), r is 1–1000, and R' is a polymer of up to 100,000 Daltons, with the amides bonded to the polymer through the carboxylic acid groups.

When $M^+$ is a metal ion, it may include ions of metals such as alkali metals, e.g., Li, Na, K, Rb, and Cs; alkaline earth metals, e.g., Be, Ca, Ba, Sr, and Mg; Group Ib metals, e.g., Ga, In, and the Lanthanide elements (57–71); Group IV metals, e.g., Ti, Zr, Hf, Ge, and Sn; Group V metals, e.g., V, Nb, and Ta; Group VI metals, e.g., Cr, Mo, and W; Group VIIa metals, e.g., Mn, Tc, and Re; and Group VIII metals, e.g., Fe, Co, Ni, Ru, Rh, Pd, Os, Ir, and Pt. Of the foregoing metal ions, Li, Na, K, Ba, and Mg are preferred metal ions used in the N(alkoxy-carbonyl)N-nitroamide salt reactant.

When the $M^+$ ion is a 1–2 nitrogen-containing cation, it may have the formula $R_kH_mN_x^+$, wherein $x=1$ to 2, $k=0$ to $3+x$, $m=3+x-k$, and each R is the same or different 1–6 carbon straight chain or branched alkyl. Examples of such ions include $NH_4^+$, $CH_3NH_3^+$, $(CH_3)_2NH_2^+$, $(CH_3)_3NH^+$, $(CH_3)_4N^+$, $C_2H_5NH_3^+$, $(C_2H_5)_2NH_2^+$, $(C_2H_5)_3NH^+$, $(C_2H_5)_4N^+$, $(C_2H_5)(CH_3)NH_2^+$, $(C_2H_5)(CH_3)_2NH^+$, $(C_2H_5)_2(CH_3)_2N^+$, $(C_3H_7)_4N^+$, $(C_4H_9)_4N^+$, $N_2H_5^+$, $CH_3N_2H_4^+$, $(CH_3)_2N_2H_3^+$, $(CH_3)_3N_2H_2^+$, $(CH_3)_4N_2H^+$, $(CH_3)_5N_2^+$, etc.

Other nitrogen-containing cations which may comprise $M^+$ include guanidium $(C(NH_2)_3^+)$ and a 1–10,000 nitrogen polymer of ethyleneimine, if an appropriately low reaction temperature is used.

Examples of ammonium salts of such N(alkoxycarbonyl)N-nitroamides (when R is a 1–20 carbon alkyl) include ammonium N-nitrourethane having the formula $NH_4^+N_2CO_4C_2H_5^-$ and ammonium N-nitromethylcarbamate having the formula $NH_4^+N_2CO_4CH_3^-$. Examples of polymers containing multiple N(alkoxycarbonyl)N-nitroamide groups thereon which may be used as the poly N(alkoxycarbonyl)N-nitroamide reactant include O-carbamylated polyglycidols, O-carbamylated polyvinylalcohols, and O-carbamylated cellulose.

b. Formation of The Salt or Free Acid N (alkoxycarbonyl) N-nitroamide Reactant Formation of the N(alkoxycarbonyl)N-nitroamide salt reactant, when the reactant is an ammonium salt, such as ammonium N-nitrourethane or ammonium N-nitromethylcarbamate, is described in Inorganic Synthesis, Volume 1, pages 68–74.

Alternatively, in accordance with one aspect of the invention, the salt or free acid N(alkoxycarbonyl)N-nitroamide reactant may be prepared by first mixing the corresponding alkylcarbamate with an anhydride of one or more 1-20 carbon organic acids, e.g., acetic anhydride, or an anhydride of a 1-20 carbon halo-organic anhydride, e.g., trifluoroacetic anhydride, followed by reaction with nitric acid (by dropwise addition of the nitric acid to the mixture), followed by the addition of the appropriate base (when the salt is desired rather than the free acid) until the reaction mass reaches a pH of from about 7 to about 10. The reaction is carried out within a temperature range of from about $-10°$ C. to about $30°$ C., preferably about $20°$ C. for a period of at least about 8 hours.

In a preferred embodiment the alkylcarbamate and the anhydride are first mixed together by dissolving the reactants in an aprotic solvent, such as methylene chloride or acetonitrile (or other aprotic solvents mentioned below), followed by addition of the nitric acid to the reaction mass. The N(alkoxycarbonyl)N-nitroamide, e.g., N-nitrourethane, may then be treated with the appropriate base to form the salt, i.e., treated with ammonia to form the corresponding ammonium N(alkoxycarbonyl)N-nitroamide, e.g., ammonium N-nitrourethane. The ammonium N(alkoxy-carbonyl)N-nitroamide can also be generated by addition of one equivalent of ammonium acetate, along with ethyl alcohol solvent, to the alkyl N-nitrocarbamate.

Alternatively, the organic acid anhydride may be first mixed with the nitric acid, followed by reaction with the alkylcarbamate, followed by reaction with the base to form the salt.

c. The Nitronium-Containing Compound

By use of the term "nitronium-containing compound" is meant a covalently bonded compound containing a $NO_2-$ group such as, for example, covalent $N_2O_5$ ($NO_2NO_3$) or trifluoroacetylnitrate; a nitryl halide such as $FNO_2$; or a nitronium salt having the formula $(NO_2^+)_1 X^{-q}$, where X is the anion of the nitronium salt and $q=1-2$.

Examples of anions of such nitronium salts which may be used as reactants with the N(alkoxycarbonyl)N-nitroamide reactant to form the desired dinitramide salts include $BF_4^-$, $NO_3^-$, $HS_2O_7^-$, $AlCl_4^-$, $F^-$, $PF_6^-$, $ClS_2O_6^-$, $F_2PO_2^-$, $AsF_6^-$, $SbF_6^-$, $FS_2O_6^-$, $ClO_4^-$, $S_2O_7^{-2}$, $SiF_6^{2}$, and $SO_3F^-$.

As will be discussed below, the nitronium-containing compound is preferably formed, dissolved, dispersed, or mixed in a liquid prior to introduction into the reaction chamber, or formed in the chamber. If the particular nitronium-containing compound is soluble in the particular liquid used, the particle size of the nitronium-containing compound is, of course irrelevant. However, if a dispersion or mixture is to be formed, the size of the nitronium-containing compound may vary from as small as colloidal to as large as 1000 microns or higher. However, it will be understood that larger surface areas, i.e., smaller particles sizes, are the most desirable to facilitate reaction between the N(alkoxycarbonyl)N-nitroamide in solution and the nitronium-containing reactant.

If the nitronium-containing compound is used in the reaction in solid form, i.e., not in a liquid as a solution, dispersion, or mixture, as will be discussed in the alternate embodiment below, the particle size of the nitronium-containing compound should preferably range from about 50 Angstroms to about 1000 microns.

The content of $NO^+$, NO, and/or $NO_2$, or any other impurity in the nitronium-containing compound should not collectively exceed more than 10 wt. % of the total weight of the nitronium-containing compound. The presence of these particular oxides of nitrogen may interfere with the reaction, resulting in a reduced yield and a possible increase in side products. Therefore, the reactants used in the process of the invention should be made or purified to provide a total content of $NO^+$, NO, and/or $NO_2$ of less than 10 wt. %.

d. Solution/Dispersion/Mixture formed with Aprotic Liquid

In the preferred embodiment of the process, the first step is to form a solution, dispersion, or mixture of the nitronium-containing compound in a non-reactive aprotic liquid or solvent, i.e., a liquid that does not yield or accept a proton. The purpose of forming such a solution, dispersion, or mixture of the nitronium-containing compound, which will normally be in solid form, with the aprotic liquid, is to facilitate contact between the N(alkoxycarbonyl)N-nitroamide salt or acid reactant and the nitronium-containing reactant, i.e., the aprotic liquid does not enter into the reaction.

The aprotic liquid or solvent must be capable of existing in the liquid state at the temperature and pressure used in the reaction between the salt or acid N(alkoxycarbonyl)N-nitroamide reactant and the nitronium-containing reactant. Examples of aprotic liquids which may be used in the process of the invention include methylene chloride ($CH_2Cl_2$), chloroform ($CHCl_3$), carbon tetrachloride ($CCl_4$), methyl ether (($CH_3)_2O$), any freon gas (including fluorocarbons and chlorofluorocarbons), acetonitrile, ethyl acetate, ethyl ether, tetrahydrofuran, sulfolane, or mixtures of same.

The nitronium-containing reactant is dissolved, dispersed, or merely added to the aprotic liquid in an amount ranging from about 1 to about 50 wt. % of the total weight of the resulting solution, dispersion, or mixture of the nitronium-containing compound and aprotic liquid, and preferably in an amount ranging from about 10 to about 25 wt. % of the resulting solution, dispersion, or mixture.

e. Reaction Conditions to Form Intermediate Product

The reaction between the N(alkoxycarbonyl)N-nitroamide reactant and the nitronium-containing reactant is carried out at a temperature of from about $+60°$ C. to about $-120°$ C., preferably from about $0°$ C. to about $-90°$ C., and most preferably from about $-20°$ C. to about $-80°$ C.

From a standpoint of economics, of course, use of higher temperatures within the stated ranges will be most desirable anyway. In some instances, the lower end of the temperature range will be determined by the freezing temperature of the solution, dispersion, or mixture of the aprotic liquid and the nitronium-containing compound.

The pressure in the reactor during the reaction between the N(alkoxycarbonyl)N-nitroamide reactant and the nitronium-containing reactant may range from slightly lower than atmospheric, i.e., about 700 Torr to slightly above atmospheric, i.e., about 800 Torr, but will typically be at about atmospheric pressure.

The reaction should be carried out under anhydrous conditions which may normally be provided by providing a blanket of inert or non-reactive gas such as argon or nitrogen. The use of oxygen or dry air may also be acceptable, but is not preferred.

The reaction is preferably carried out while mechanically stirring the liquid in the reaction vessel sufficiently to avoid any settling (when the nitronium compound is not dissolved) so that the nitronium-containing compound is always exposed to the N(alkoxycarbonyl)N-nitroamide reactant.

The reaction may be carried out as a batch process or on a continuous basis with batch or continuous extraction of portions of the reaction mass. When the reaction is carried out on a batch basis, it may be carried out for a period of from about 0.5 to about 8 hours, i.e., the reaction temperature is maintained, the N(alkoxycarbonyl)N-nitroamide and nitronium-containing reactants are added to the reactor, and stirring is continued for this period of time.

f. Reaction of Intermediate Product With Base or Alcohol to Form Corresponding Dinitramide Salt or Acid The intermediate product formed by the reaction between the N(alkoxycarbonyl)N-nitroamide reactant and the nitronium-containing reactant is then reacted with a base or alcohol to respectively form the corresponding dinitramide salt or dinitramidic acid, both having the general formula $M^{+n}(N(NO_2)_2^-)_n$, where M is selected from the group consisting of a metal ion, hydrogen, and a nitrogen-containing cation having from 1 to 8 nitrogen atoms and n is the cationic charge of M, usually 1–3, as previously defined.

When the $M^{+n}$ ion, in the formula $M^{+n}(N(NO_2)_2^-)_n$ of the final dinitramide product, is a metal ion, a base containing one of the previously defined metals is reacted with the intermediate product. For example, the hydroxide (or acetate, as appropriate) of the particular metal is reacted with the intermediate product to form the desired metal dinitramide salt, e.g., sodium hydroxide is reacted with the intermediate product to form sodium dinitramide $(Na^+N(NO_2)_2^-)$.

When the $M^{+n}$ ion, in the formula $M^{+n}(N(NO_2)_2^-)_n$ of the final dinitramide product, is hydrogen, i.e., when the acid form of the dinitramide is desired, the intermediate product can be reacted with an alcohol, such as ethyl alcohol, to form the dinitramidic acid $(H^+N(NO_2)_2^-)$.

When the $M^{+n}$ ion, in the formula $M^{+n}(N(NO_2)_2^-)_n$ of the final dinitramide product, is a nitrogen-containing cation, a base containing or comprising the appropriate nitrogen-containing moiety is reacted with the intermediate product, e.g., ammonia $(NH_3)$ is reacted with the intermediate product to form ammonium dinitramide $(NH_4^+(N(NO_2)_2^-))$. Whenever the $M^{+n}$ ion in the final dinitramide product differs from the $M^{+n}$ ion in the N(alkoxycarbonyl)N-nitroamide reactant, the intermediate product should be separated from the byproducts of the reaction of the N(alkoxycarbonyl)N-nitroamide reactant and the nitronium-containing reactant prior to reacting the intermediate product with the base or alcohol to form the desired final dinitramide product.

g. Reaction Equations

The reaction to form the N(alkoxycarbonyl)N-nitroamide reactant, when the ammonium salt of the N(alkoxycarbonyl)N-nitroamide reactant is formed using acetic anhydride, may be represented by the following equations:

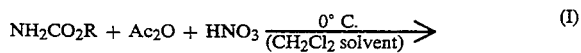

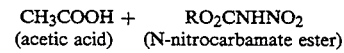

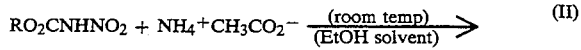

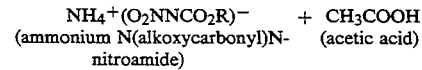

The reaction between the N(alkoxycarbonyl)N-nitroamide reactant and the nitronium-containing reactant to form the intermediate product (when the nitronium-containing reactant comprises a nitronium tetrafluoroborate salt and the N(alkoxycarbonyl)N-nitroamide reactant comprises ammonium N-nitrourethane), may be represented by the following equation:

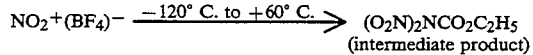

This intermediate product is then reacted with a base to form the corresponding dinitramide salt, or with an alcohol to form the corresponding dinitramidic acid. The reaction with a base to form the dinitramide salt (when $NH_3$ is the base and the intermediate product is the product of equation (III) above) can be represented by the following formula:

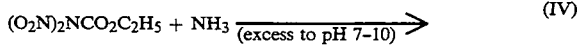

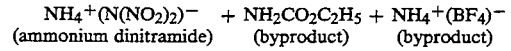

The reaction of an alcohol with the intermediate product of equation (III) to form the dinitramidic acid (when ethyl alcohol is used), may be illustrated by the following equation:

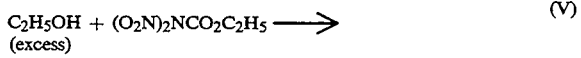

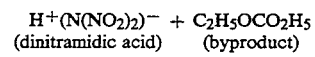

h. Separation and Recovery of Dinitramide Salt Reaction Product

The dinitramide salt product may be extracted and separated from the carbamate byproduct and other byproducts by solvent extraction. Typical solvents which may be used for such solvent extraction include acetone, acetonitrile, isopropanol, t-butanol, ethyl acetate, tetrahydrofuran, and $CH_3(CH_2)_nOH$, where $n=0-7$, or mixtures of the above solvents. The dinitramide salt can also be extracted by solutions of ammonia in chlorinated hydrocarbons such as $CH_2Cl_2$, $CHCl_3$, $CCl_4$, or $CHCl_2CHCl_2$ to cause the desired dinitramide salt product to dissolve, as well as a mixture of ethyl acetate and n-butanol. The carbamate byproduct separated from the dinitramide salt product may be purified and reused.

If it is desired to form the ammonium salt of the dinitramide, the reaction mixture may be maintained under a basic condition by maintaining a blanket of ammonia gas over the reaction mixture.

The extracted dinitramide salt product is precipitated by addition of a material which will reduce the solubility of the dinitramide, i.e., cause it to precipitate, for example, by the addition of chloroform. The product is then filtered off and the product may then dried in vacuo, using a vacuum ranging from about 0.1 to 20 Torr, to evaporate the solvents to obtain the desired dinitramide product.

The dried product residue may then be redissolved and recrystallized in any suitable solvent such as n-butanol or another alcohol solvent, by dissolving the residue with heating in the solvent and then cooling the solvent until the dinitramide salt precipitates. For example, when n-butanol is used as the solvent, from about 5 to about 15 milliliters of n-butanol per gram of residue is used to dissolve the residue upon heating to about 60° C. to about 80° C. after which the solution is cooled to about $-15°$ C. and chloroform is added to precipitate the dinitramide salts as white crystals. In some instances, impurities crystallize out first and then are separated from the solution before further cooling. Other suitable solvents which can be used for recrystallization of the dinitramide salt product include $CH_3CN$, ethyl acetate, 2-6 carbon alcohols, methylethyl ketone, and nitromethane.

The crude product can be purified by elution through a column containing 3-15 times the weight of the product of 230-400 mesh silica gel, eluting with acetonitrile.

i. Formation of Nitronium-Containing Compound

The reactions used to form the various nitronium-containing compounds useful as reactants in the process of the invention are well known and form no part of the invention per se. As representative examples of how to form the nitronium-containing compounds used in the practice of this invention, nitronium tetrafluoroborate may be formed by the slow addition of $BF_3$ to a solution of HF and ethyl-nitrate in methylene chloride. Nitronium nitrate ($NO_2NO_3$) may be formed by the ozonolysis of $N_2O_4$ by passing ozone through a stirred solution of $N_2O_4$ in $CH_2Cl_2$. Nitronium hydrogen disulfate may be made by adding $2SO_3$ to one equivalent of anhydrous $HNO_3$ in dry $CH_2Cl_2$.

The following examples will serve to further illustrate the process of the invention.

Example I

To form the ammonium N-nitrourethane reactant, 100 millimoles (mmol) of acetic anhydride and 110 mmol of urethane ($NH_2CO_2C_2H_5$) were dissolved in 40 milliliters (ml) of $CHCl_3$, cooled to 0° C. under argon, and treated with 100 mmol (6 grams) of 100% $HNO_3$. This mixture was stirred overnight and allowed to warm to room temperature. A colorless solution resulted.

At this point in the preparation, two different procedures were used. First, 100 ml (8 grams) of ammonium acetate, along with 40 ml of ethyl alcohol, were added to the colorless solution. The mixture was stirred 12 hours and filtered to give 14 grams of pure N-nitrourethane product.

Using a second procedure, 100 ml of $Cl_2HCCHCl_2$ was added to the solution and the solution was then concentrated in vacuo to about 25 ml. 200 ml of $CHCl_3$ was then added, the solution was cooled in ice, made basic by the addition of ammonia gas, filtered, and the precipitate was dried in vacuo. The resulting ammonium N-nitrourethane had a slight yellow color with a yield of 14.6 grams (96%). Similar results were obtained by first mixing the acetic anhydride with the nitric acid at 0° C. followed by the addition of urethane at 0° C., except that the resulting product was less pure.

Example II $NO_2NO_3$ was prepared by the ozonolysis of $N_2O_4$ by dissolving 45 mmol of $N_2O_4$ in 200 ml. of dry $CH_2Cl_2$, cooling the solution to $-78°$ C., and bubbling ozone through the solution, while stirring and allowing the solution to warm up to $-30°$ C., until the solution was dark blue, indicating that all of the $N_2O_4$ had been converted to $N_2O_5$.

This solution was then added to a suspension of 7.5 grams (49.7 mmoles) of the ammonium N-nitrourethane prepared in Example I and suspended in 200 ml of methylene chloride which had been previously cooled to $-50°$ C. before the addition. The reaction was allowed to proceed for one hour, warming to $-30°$ C. over that hour. Excess ammonia gas was then added to raise the pH to 10. The solution was then filtered and the insoluble material was collected and digested 20 min in 150 ml of acetonitrile. The resulting suspension was filtered, and the filtrate was passed through a $4'' \times 1''$ column of 230-400 mesh silica-gel, eluting with $CH_3CN$. The filtrate was concentrated to 30 ml and treated with 30 ml $CHCl_3$, resulting in the precipitation of 4.0 g of pure crystalline ammonium dinitramide mp 90–93° (60% yield).

EXAMPLE III 2m moles of ammonium N-nitrourethane, made in accordance with the procedure of Example I, was suspended in 10 ml. of $CH_3CN$, cooled to approximately $-40°$ C., and then treated with 2 mmoles of nitronium tetrafluoroborate. The reaction mixture was stirred for about 10 minutes and excess ammonia gas was then added until the pH of the reaction mixture reached approximately 9. The solution was then concentrated to about 3 ml. and then 20 ml. of ethyl acetate was added and stirred into the mixture for about 5 minutes. The solution was then filtered, the filtrate was concentrated down to about 3 ml., and 20 ml. of $CHCl_3$ was added to precipitate the product. The precipitated ammonium dinitramide salt was filtered off and then dried in vacuo. The yield of ammonium dinitramide was 96 mg., or approximately 40% based on the starting amount of $NO_2BF_4$.

EXAMPLE IV

Ammonium N(methoxycarbonyl)N-nitroamide (ammonium N-nitromethylcarbamate) was prepared by suspending 1.05 moles of methylcarbamate in 400 ml. of $CHCl_3$ cooled in an ice bath under an argon atmosphere. This suspension was treated with 1 mole of acetic anhydride followed by a slow dropwise addition of 1 mole of 98% $HNO_3$. The reaction temperature got as high as 25° C. with continuous ice bath cooling of the reaction vessel. The reaction mass was stirred overnite and the temperature was allowed to slowly rise to room temperature. To the reaction mixture was added 0.5 L. of chlorobenzene and the reaction mixture was then evaporated down to 300 ml. of total volume in a rotary evaporator. Another 0.5 L. of chlorobenzene and 100 ml. of methanol were added to the reaction mixture to dissolve the precipitated solid N(methoxycarbonyl)N-nitroamide.

The resulting solution was concentrated to dryness at 50° C. under vacuum in an effort to completely remove acetic acid which can contaminate the product. The N(methoxycarbonyl)N-nitroamide product was isolated as solid crystals. The solid crystals were suspended in 600 ml. of $CHCl_3$, solubilized with 100 ml. of methanol, cooled in an ice bath, and treated with ammonia to give a resulting solution having a pH of 8, during which a temperature rise was observed from the reaction of ammonia with the N(methoxycarbonyl)N-nitroamide.

A heavy precipitate formed and the reaction mixture was then cooled in an ice bath. This precipitate was collected by filtration, washed with $CHCl_3$, and the solid was then dried in a vacuum of about 10 milliTorr. The yield of ammonium N(methoxycarbonyl)N-nitroamide product was about 122 grams or 85%.

EXAMPLE V

A suspension/solution of 100 mmoles of $N_2O_5$ in 175 ml. of $CH_2Cl_2$ was prepared by ozonolysis of $N_2O_4$ at $-60°$ C. This suspension was diluted by adding 60 ml. of $CH_3CN$, cooled to $-78°$ C., and 100 mmoles (13.7 grams) of the ammonium N(methoxycarbonyl)N-nitroamide (ammonium N-nitromethylcarbamate) made in Example IV was added to the reaction mixture. The mixture was then stirred for 1 hour while it was allowed to slowly warm to $-60°$ C. over that hour. Excess ammonia gas was then added until the pH reached 9. A thick precipitate developed. The reaction mass was concentrated in vacuo in a rotary evaporator, and 100 ml. of $CH_3CN$ and 100 ml. of ethylacetate were then added. The reaction mixture was then filtered and then washed with ethylacetate. The filtrate was then concentrated to approximately 30 ml. and 200 ml. of $CHCl_3$ was then added to precipitate the product from the filtrate. The solid ammonium dinitramide product was then filtered and collected. The product was then dried in vacuo to yield 6.4 grams (52%) of ammonium dinitramide salt.

Thus the process of the invention provides a method for forming an ionically bonded dinitramide salt by reaction of a salt or free acid of an N(alkoxycarbonyl)N-nitroamide with a nitronium-containing compound such as a nitronium salt at a temperature range of from about $+60°$ C. to about $-120°$ C. followed by reaction with a base to form the desired dinitramide salt. The N(alkoxycarbonyl)N-nitroamide reactant may be made by mixing an alkyl carbamate with the anhydride of one or more 1–2 carbon organic acids followed by stepwise reaction with nitric acid, and then reaction with an appropriate base, if the free acid is not desired.

Having thus described the invention what is claimed is:

1. A process for the formation of a dinitramide salt having the formula $M^{+n}(N(NO_2)_2^-)_n$, where M is selected from the group consisting of a metal ion, hydrogen, and a nitrogen-containing cation having from 1 to 8 nitrogen atoms and n is the cationic charge of M, which comprises:
   (a) reacting an N(alkoxycarbonyl)N-nitroamide reactant with a nitronium-containing compound; and
   (b) treating the reaction mixture with a base to form the dinitramide salt.

2. The process of claim 1 wherein said N(alkoxycarbonyl)N-nitroamide reactant has the formula: $M^{+n}((O_2NNCO_2R)^-)_n$, where M is selected from the group consisting of a metal ion, hydrogen, and a nitrogen-containing cation having from 1 to 8 nitrogen atoms, n is the cationic charge of M, and R is selected from the group consisting of a 1–20 carbon branched or straight chain alkyl and a 1–20 carbon branched or straight chain fluoroalkyl.

3. The process of claim 1 wherein said metal ion is selected from the group of metals consisting of alkali metals, Li, Na, K, Rb, and Cs; alkaline earth metals, Be, Ca, Ba, Sr, and Mg; Group Ib metals, Ga, In, and the Lanthanide elements (57–71); Group IV metals, Ti, Zr, Hf, Ge, and Sn; Group V metals, V, Nb, and Ta; Group VI metals, Cr, Mo, and W; Group VIIa metals, Mn, Tc, and Re; and Group VIII metals, Fe, Co, Ni, Ru, Rh, Pd, Os, Ir, and Pt.

4. The process of claim 1 wherein said metal ion is selected from the group of metals consisting of Li, Na, K, Ba, and Mg.

5. The process of claim 1 wherein said $M^+$ ion is a 1–2 nitrogen-containing cation, it may have the formula wherein $x=1$ to 2, $k=0$ to $3+x$, $m=3+x-k$, and each R is the same or different 1–6 carbon straight chain or branched alkyl.

6. The process of claim 1 wherein said $M^+$ ion is a cubane-1,4-bis ammonium ion selected from the group consisting of a cubane-1,2,4,7-tetra ammonium ion; a cubane-1,3,5,7-tetra ammonium ion; a cubane-1,2,3,4,-tetra ammonium ion; a cubane-1,2,3,4,7-penta ammonium ion; and a cubane-1,2,4,6,8-penta ammonium ion.

7. The process of claim 1 wherein said $M^+$ ion is selected from the group consisting of guanidium ($C(NH_2)_3^+$); triaminoguanidinium ($C(N_2H_3)_3^+$); nitronium ($O=N=O^+$); and nitrosonium ($N=O^+$).

8. The process of claim 1 wherein said N(alkoxycarbonyl)N-nitroamide reactant is a salt having the formula: $(M^{+n}((O_2NNCO_2)^-)_n)_r^{R'}$, where M is selected from the group consisting of a metal ion, n is the cationic charge of M, r is 1–1000, and a nitrogen-containing cation having from 1 to 8 nitrogen atoms, and R' is a polymer of up to 100,000 Daltons.

9. The process of claim 1 wherein said nitronium-containing compound is selected from the group consisting of a covalently bonded compound containing a $NO_2-$ group, a nitryl halide, and a nitronium salt having the formula $(NO_2^+)_nX^{-n}$, where X is the anion of the nitronium salt and $n=1-2$.

10. The process of claim 1 wherein said reaction to form said dinitramide salt is carried out at a temperature ranging from about $+60°$ C. to about $-120°$ C.

11. The process of claim 10 wherein said reaction temperature to form said dinitramide salt ranges from about 0° C. to about $-90°$ C.

12. A process for the formation of an ammonium dinitramide salt having the formula $NH_4^+N(NO_2)_2^-$, which comprises reacting an N(alkoxycarbonyl)N-nitroamide with a nitronium-containing compound followed by addition of ammonia.

13. The process of claim 12 wherein said alkyl in said N(alkoxycarbonyl)N-nitroamide is selected from the group consisting of a 1-20 carbon branched or straight chain alkyl and a 1-20 carbon branched or straight chain fluoroalkyl.

14. The process of claim 13 wherein said N(alkoxycarbonyl)N-nitroamide is formed by the steps of:
 (a) mixing an alkylcarbamate with an anhydride of one or more 1-20 carbon organic acids; and
 (b) then reacting the resulting mixture with nitric acid.

15. The process of claim 14 wherein a salt of said N(alkoxycarbonyl)N-nitroamide is formed by the additional step of reacting said N(alkoxycarbonyl)N-nitroamide with a base.

16. The process of claim 12 wherein said alkyl in said N(alkoxycarbonyl)N-nitroamide salt is a polymer of up to 100,000 Daltons.

17. The process of claim 12 wherein said nitronium-containing compound is selected from the group consisting of a covalently bonded compound containing a $NO_2-$ group, a nitryl halide, and a nitronium salt having the formula $(NO_2^+)_q X^{-q}$, where X is the anion of the nitronium salt and $q = 1-2$.

18. A process for the formation of an ammonium dinitramide salt having the formula $NH_4^+N(NO_2)_2^-$, which comprises reacting an N(alkoxycarbonyl)N-nitroamide reactant selected from the group consisting of N(methoxycarbonyl)N-nitroamide and N(ethoxycarbonyl)N-nitroamide with a nitronium-containing reactant to form an intermediate product; followed by reacting the intermediate product with ammonia.

19. The process of claim 18 wherein said nitronium-containing reactant is selected from the group consisting of nitronium nitrate ($NO_2NO_3$), nitryl fluoride ($FNO_2$), and nitronium tetrafluoroborate ($NO_2^+BF_4^-$).

20. The process of claim 18 wherein said reaction to form said ammonium dinitramide salt is carried out at a temperature ranging from about $+60°$ C. to about $-120°$ C.

21. The process of claim 18 wherein said N(alkoxycarbonyl)N-nitroamide reactant is formed by the steps of:
 (a) mixing an alkylcarbamate selected from the group consisting of methylcarbamate and ethylcarbamate with acetic anhydride; and
 (b) then adding nitric acid to the resulting mixture.

22. The process of claim 21 wherein an ammonium N(alkoxycarbonyl)N-nitroamide reactant is then formed by the addition of $NH_3$ to the reaction mixture.

23. The process of claim 21 wherein an ammonium N(alkoxycarbonyl)N-nitroamide reactant is then formed by the addition of ammonium acetate to the reaction mixture.

24. The process of claim 21 wherein said reaction to form said N(alkoxycarbonyl)N-nitroamide reactant is carried out at a temperature ranging from about $-30°$ C. to about $30°$ C.

25. A process for the formation of an ammonium dinitramide salt having the formula $NH_4^+N(NO_2)_2^-$, which comprises:
 (a) forming an ammonium N(alkoxycarbonyl)N-nitroamide salt selected from the group consisting of ammonium N(methoxycarbonyl)N-nitroamide and ammonium N(ethoxycarbonyl)N-nitroamide at a temperature ranging from about $-30°$ C. to about $30°$ C. by the steps of:
  (i) first mixing an alkylcarbamate selected from the group consisting of methylcarbamate and ethylcarbamate with acetic anhydride;
  (ii) then adding nitric acid to the resulting mixture; and
  (iii) then adding $NH_3$ to the reaction mixture; and
 (b) then reacting said ammonium N(alkoxycarbonyl)N-nitroamide with a nitronium-containing compound selected from the group consisting of nitronium nitrate ($NO_2NO_3$), nitryl fluoride ($FNO_2$), and nitronium tetrafluoroborate ($NO_2^+BF_4^-$) at a temperature ranging from about $+60°$ C. to about $-120°$ C.; and
 (c) then contacting the reaction mass with $NH_3$ to form said ammonium dinitramide salt.

26. A process for the formation of ammonium dinitramide salt having the formula $NH_4^+N(NO_2)_2^-$, which comprises:
 (a) reacting together, at a temperature ranging from about $+60°$ C. to about $-120°$ C., an ammonium N(alkoxycarbonyl)N-nitroamide selected from the group consisting of ammonium N(methoxycarbonyl)N-nitroamide and ammonium N(ethoxycarbonyl)N-nitroamide with a nitronium-containing reactant selected from the group consisting of nitronium nitrate ($NO_2NO_3$), nitryl fluoride ($FNO_2$), and nitronium tetrafluoroborate ($NO_2+BF_4{}_{hu\ -}$); and
 (b) then contacting the reaction mass with $NH_3$ to form said ammonium dinitramide salt.

27. The process of claim 26 wherein said ammonium N(alkoxycarbonyl)N-nitroamide reactant consists essentially of ammonium N(methoxycarbonyl)N-nitroamide.

28. The process of claim 26 wherein said ammonium N(alkoxycarbonyl)N-nitroamide reactant consists essentially of ammonium N(ethoxycarbonyl)N-nitroamide.

29. The process of claim 26 wherein said nitronium-containing reactant consists essentially of nitronium nitrate ($NO_2NO_3$).

30. The process of claim 26 wherein said nitronium-containing reactant consists essentially of nitronium tetrafluoroborate ($NO_2^+BF_4^-$)

31. A process for the formation of dinitramidic acid having the formula $H^+N(NO_2)_2^-$ which comprises:
 (a) reacting an N(alkoxycarbonyl)N-nitroamide reactant with a nitronium-containing compound; and
 (b) treating the reaction mixture with an alcohol to form dinitramidic acid.

* * * * *

UNITED STATES PATENT AND TRADEMARK OFFICE
CERTIFICATE OF CORRECTION

PATENT NO. : 5,415,852  
DATED : May 16, 1995  
INVENTOR(S) : Robert J. Schmitt, Jeffrey C. Bottaro, Paul E. Penwell, and David C. Bomberger Page 1 of 2

It is certified that error appears in the above-identified patent and that said Letters Patent is hereby corrected as shown below:

Col. 1, line 49, after "related" and before "application" add "U.S. patent".

Col. 1, line 62, after "related" and before "application" add "U.S. patent".

Col. 1, line 63, after "1990", add ", now issued as U.S. Patent 5,198,204 on March 30, 1993,".

Col. 2, line 9, after "related" and before "application", add "U.S. patent".

Col. 2, line 9, change "07/737 757" to "07/737,757".

Col. 3, line 50, change "$(C_{25})_4N^+$" to "$(C_2H_5)_4N^+$".

Col. 3, line 61, change "8penta" to "8-penta".

Col. 3, line 64, change "$(C(N_2)_3^+)$" to "$(C(NH_2)_3^+)$".

Col. 4, line 8, change "+60°C." to "0°C.".

Col. 5, line 51, change "$(NO_2^+)_1 X^{-q}$" to "$(NO_2^+)_q X^{-q}$".

Col. 5, line 58, change "$SiF_6^{2}$" to "$SiF_6^{-2}$".

Col. 7, line 51, change "$(Na^+N(NO_2)_{2-})$" to "$(Na^+N(NO_2)_2^-)$".

Col. 8, line 61, change "$C_2H_5OCO_2H_5$" to "$C_2H_5OCO_2C_2H_5$".

Col. 10, line 41, change "CH3CN" to "$CH_3CN$".

Col. 10, line 48, change "2m moles" to "2 mmoles".

Col. 11, line 5, change "HNO3" to "$HNO_3$".

UNITED STATES PATENT AND TRADEMARK OFFICE
CERTIFICATE OF CORRECTION

PATENT NO. : 5,415,852

DATED : May 16, 1995

INVENTOR(S) : Robert J. Schmitt, Jeffrey C. Bottaro, Paul E. Penwell, and David C. Bomberger It is certified that error appears in the above-identified patent and that said Letters Patent is hereby corrected as shown below:

Col. 12, line 36, claim 5, after "formula", add "$R_k H_m N_x^+$, ".

Col. 12, line 53, claim 8, change "$(M^{+n}((O_2NNCO_2)^-)_n)_r R$" to "$(M^{+n}((O_2NNCO_2)^-)_n)_r R'$".

Col. 14, line 38, claim 26, change "$(NO_2+BF_{4hu-})$" to "$(NO_2^+ BF_4^-)$".

Col. 14, line 55, claim 30, at the end of the claim, add ".".

Signed and Sealed this

Seventh Day of November, 1995

BRUCE LEHMAN

*Attest:*

*Attesting Officer*   Commissioner of Patents and Trademarks